United States Patent [19]

Montgomery

[11] 4,128,595

[45] Dec. 5, 1978

[54] ACETYLENE HYDROGENATION IN LIQUID PHASE WITH A LIQUID HYDROCARBON REACTION MEDIUM

[75] Inventor: Dean P. Montgomery, Bartlesville, Okla.

[73] Assignee: Phillips Petroleum Company, Bartlesville, Okla.

[21] Appl. No.: 792,734

[22] Filed: May 2, 1977

[51] Int. Cl.² ............................................... C07C 11/04
[52] U.S. Cl. ................................................ 260/677 H
[58] Field of Search ......................... 260/677 H, 681.5

[56] References Cited

FOREIGN PATENT DOCUMENTS

| | | | |
|---|---|---|---|
| 243868 | 4/1960 | Australia | 260/677 H |
| 1063378 | 3/1967 | United Kingdom | 260/677 H |
| 1263173 | 2/1972 | United Kingdom | 260/677 H |

*Primary Examiner*—George Crasanakis

[57] ABSTRACT

A process for the selective hydrogenation of acetylene present in acetylene-rich gases which comprises carrying out the hydrogenation in the presence of a liquid phase inert hydrocarbon reaction medium and a metal hydrogenation catalyst.

5 Claims, No Drawings

ACETYLENE HYDROGENATION IN LIQUID PHASE WITH A LIQUID HYDROCARBON REACTION MEDIUM

This invention relates to the selective hydrogenation of acetylene present in gas streams. In accordance with another aspect, this invention relates to the selective hydrogenation of acetylene in gaseous streams containing same by carrying out the hydrogenation in an inert hydrocarbon reaction medium. In accordance with another aspect, an acetylene-rich gas is dissolved in an inert hydrocarbon reaction medium, then selectively hydrogenated to ethylene in the presence of a Group VIII metal hydrogenation catalyst. In a more specific aspect, this invention relates to the catalytic process for the selective hydrogenation of acetylenic impurities contained in olefin streams by carrying out the hydrogenation in an inert paraffinic hydrocarbon reaction medium.

The selective hydrogenation of acetylene(s) present in various gaseous streams in the presence of catalysts is known in the art. It is also known in the art to carry out the hydrogenation in polar solvents. It has been observed, however, that many of the prior art methods for carrying out the selective hydrogenation have been unsatisfactory, for one reason or another, and many have not been commercially feasible. Accordingly, the present invention relates to an improved process for the selective hydrogenation of acetylenes whereby many of the disadvantages of the prior art processes are obviated.

Accordingly, an object of this invention is to provide a selective hydrogenation process for the hydrogenation of acetylene(s) present in various gases.

Another object of this invention is to provide a selective hydrogenation process which can be carried out at moderate operating temperatures.

A further object of this invention is to provide a hydrogenation process for selectively hydrogenating acetylene(s) in a commercially feasible manner.

A further object of this invention is to provide an improved hydrogenation process for selective hydrogenation of acetylene, whereby the metal hydrogenation catalyst performs better and lasts longer between catalyst regenerations.

Other objects and aspects, as well as the several advantages of the invention, will be apparent to those skilled in the art upon reading the specification and the appended claims.

In accordance with the invention, a process is provided for the selective hydrogenation of acetylene compounds present in gaseous hydrocarbon streams by contacting hydrocarbon gaseous streams with hydrogen and a liquid phase, saturated hydrocarbon reaction medium in the presence of a metal hydrogenation catalyst.

In accordance with one specific embodiment, an acetylene-rich gas is mixed with an inert hydrocarbon liquid, such as paraffinic hydrocarbons boiling above about 160° F. (71° C.), and selectively hydrogenated to ethylene in the presence of a Group VIII metal hydrogenation catalyst, preferably a palladium-on-alumina catalyst. The inert hydrocarbon reaction medium can be separated from the product and recycled or reused in the hydrogenation.

The invention is broadly applicable to the hydrogenation treatment of any gaseous mixture containing acetylene or acetylenic compounds. The acetylene(s) can be part of a gaseous mixture that includes other hydrocarbons, including other unsaturated hydrocarbons, e.g., olefins and the like. It is also within the scope of the invention to treat mixtures of olefins and acetylenes in addition to ethylene-acetylene, such as propylene-methyl acetylene, and butenes-ethyl acetylene, vinylacetylene, or diacetylene. Typically, the invention will be applicable to the treatment of an acetylene-ethylene mixture.

The inert hydrocarbon reaction medium that can be employed according to this invention is ordinarily a paraffinic hydrocarbon having a minimum boiling point of about 150° F. (66° C.) and a maximum boiling point of about 600° F. (316° C.). The invention is broadly applicable to any paraffinic hydrocarbon including isoparaffin hydrocarbons, as well as naphthenic hydrocarbons, or mixtures thereof, having a normal boiling point up to about 600° F. (316° C.). It is ordinarily preferred that the boiling point be above about 300° F. (149° C.) to permit use of lower reactor pressure. Lower boiling solvents such as hexane and cyclohexane can be used. One presently preferred solvent that has been used effectively was Soltrol 170 ®, which is a paraffinic solvent having a boiling range of about 424°–460° F. (218°–238° C.).

Suitable inert hydrocarbons that can be used as the reaction medium include cyclohexane, n-hexane, isohexanes, decane, hexadecane, hydrogenated propylene tetramer, decalin, and mixtures thereof.

Any catalyst well known to selectively hydrogenate acetylene can be employed by this invention. The Group VIII metal hydrogenation catalysts are the most commonly used and are presently preferred. The Group VIII metal hydrogenation catalysts are ordinarily associated with a support, such as alumina. One catalyst that has been used successfully is a low surface area granular alumina impregnated with about 0.1 weight percent palladium. Examples of other catalysts that can be used include Raney nickel, ruthenium-on-alumina, nickel arsenide-on-alumina, and the like, and mixtures thereof. The catalysts ordinarily contain a Group VIII metal in an amount ranging from about 0.01 to about 10 percent by weight of the total catalyst.

The hydrotreating conditions employed according to the invention can vary appreciably depending upon the stream being treated. Ordinarily, the temperature and pressure will be sufficient to hydrogenate at least a portion of the acetylenes contained in the feedstream. Generally, the hydrotreating process will be carried out over a temperature range of about 50° F. to about 400° F. (10° C. to 204° C.) and a pressure range of about 20 to about 2000 psia (0.14 to 14 MPa). In actual operation, the combination of temperature and pressure is such as to maintain the acetylene-saturated reaction medium in the liquid phase. Hydrogen flow, during the hydrogenation, is at least sufficient to meet the stoichiometric requirements for converting acetylene into ethylene, and, generally, is in the range of about 1–100 mols of hydrogen per mol of acetylene in the feed. Reaction time can vary from about 1 minute to about 5 hours with a preferred reaction time in the range of about 1 to 60 minutes.

The process of the invention can be carried out continuously or batchwise, and any convenient contacting apparatus can be used. The process can be carried out employing catalysts in a fixed bed, or other types of contact. Since the solubility of acetylene in the inert hydrocarbon diluent is rather low under reaction conditions, the major amount of acetylene (and product ethylene) can pass through the reactor in the vapor phase. For this reason, a trickle bed-type reactor is preferred in which the vapor feed and liquid hydrocarbon diluent are both introduced at the top of the reactor and passed cocurrently over the catalyst bed. The rate of passage of the acetylene-hydrocarbon mixture over the catalyst bed is such that the acetylenes are essentially completely converted by the time these reach the bottom of the catalyst packed column.

After completion of the reaction period, or after the reaction mixture leaves the reaction zone, the reaction mixture can be subjected to separation operations and to recovery of desired product using any conventional and suitable means. The olefin, especially ethylene, and unconverted acetylene remaining after reaction can be separated from the inert hydrocarbon reaction diluent by stripping or distillation or other suitable means.

The following example of the invention illustrates one embodiment of the invention and presents the advantages for use of the inert solvent over a polar solvent.

EXAMPLE

A reactor zone one inch (0.0254 m) I.D. by 12 inches (0.305 m) long was filled with a granular catalyst composed of a low surface area alumina impregnated with 0.1 weight percent palladium and used as a trickle bed reactor for selective hydrogenation of acetylene.

In a control run, acetylene feed rate was 1.5 SCFH (11.8 $\mu m^3/s$), DMF (dimethylformamide) solvent rate was 10 lbs/hr (1.26 g/s), and hydrogen rate was 1.5 SCFH (11.8 $\mu m^3/s$). Reactor pressure was 300 psia (2.07 MPa), and reactor temperature ranged from about 240° F. (116° C.) to 300° F. (149° C). Acetylene conversion was essentially 100 percent at the beginning of the run, but dropped to 50 percent in about 17 hours. Selectivity to ethylene averaged about 75 percent. During the run, DMF purity dropped from 99.8 to 99.1 weight percent.

In a run according to the invention, after regenerating the above catalyst by burn-off in air at 700°–900° F. (371°–482° C.), acetylene hydrogenation was resumed using Soltrol ® 170 solvent instead of DMF. Acetylene feed rate was 1.53 SCFH (12 $\mu m^3/s$), solvent rate was 4 lbs/hr (0.5 g/s), and hydrogen rate was about 2.0 SCFH (15.7 $\mu m^3/s$). Reactor pressure was 50 psia (0.345 MPa), and reactor temperature ranged from about 240° F. (116° C.) to 380° F. (193° C.). Acetylene conversion was maintained at about 99 percent for nine days with selectivity as follows:

Ethylene — 84.5%
Ethane — 3.9
$C_4+$ volatiles — 9.8
Green oil* — 1.8

*Heavies which accumulated in the solvent. As can be seen from the above runs, the same catalyst performs better and lasts longer between catalyst regenerations when an inert hydrocarbon reaction medium is used according to the invention. In the control run using DMF on a once-through basis, product selectivities were lower and conversion dropped off significantly, necessitating catalyst regeneration (burn-off) in 4 days.

I claim:

1. A process for the selective hydrogenation of acetylenic compounds in the liquid phase, which comprises contacting hydrogen and a gaseous hydrocarbon stream containing acetylene with an inert saturated liquid hydrocarbon reaction medium having a boiling range of about 150° F. (66° C.) to about 600° F. (316° C.) and with a supported catalyst comprising a Group VIII metal under hydrogenation conditions including a pressure sufficient to maintain said reaction medium in the liquid phase to hydrogenate at least a portion of the acetylenes contained in said stream.

2. A process according to claim 1 wherein said contacting is effected at a temperature in the range of about 50° F. (10° C.) to about 400° F. (204° C.), a pressure in the range of about 20 to about 2000 psia (0.14–14 MPa), an amount of hydrogen sufficient to be at least the amount needed to meet the stoichiometric requirements for converting acetylene to ethylene, and wherein the catalyst is palladium-on-alumina.

3. A process according to claim 1 wherein said hydrogenation is carried out by introducing said gaseous hydrocarbon stream with hydrogen and said liquid reaction medium at the top of a bed of said catalyst and passing said gaseous hydrocarbon stream, hydrogen and liquid reaction medium cocurrently in trickle flow downwardly through said catalyst bed.

4. A process according to claim 1 wherein said inert saturated hydrocarbon reaction medium is an isoparaffinic hydrocarbon mixture having a boiling range of about 420° F. (216° C.) to about 460° F. (238° C.) and said catalyst is palladium-on-alumina wherein the amount of palladium present ranges from about 0.01 to about 10 weight percent.

5. A process according to claim 1 wherein said stream contains acetylene and ethylene and said contacting with said catalyst being at a temperature in the range of about 50°–400° F. (10°–204° C.) in a liquid paraffinic hydrocarbon reaction medium having a boiling range from about 300° F. (149° C.) to about 600° F. (316° C.).

* * * * *